(12) United States Patent
Marsh

(10) Patent No.: US 11,244,769 B2
(45) Date of Patent: Feb. 8, 2022

(54) INTERACTIVE INTERVENTIONAL SHIELD

(71) Applicant: Brandi Tsama Marsh, Rego Park, NY (US)

(72) Inventor: Brandi Tsama Marsh, Rego Park, NY (US)

( * ) Notice: Subject to any disclaimer, the term of this patent is extended or adjusted under 35 U.S.C. 154(b) by 152 days.

(21) Appl. No.: 16/779,952

(22) Filed: Feb. 3, 2020

(65) Prior Publication Data

US 2021/0280333 A1 Sep. 9, 2021

Related U.S. Application Data

(60) Provisional application No. 62/922,088, filed on Jul. 24, 2019.

(51) Int. Cl.
| | |
|---|---|
| *G21F 7/04* | (2006.01) |
| *G21F 7/03* | (2006.01) |
| *A61B 6/10* | (2006.01) |
| *G21F 3/00* | (2006.01) |
| *G21F 1/12* | (2006.01) |

(52) U.S. Cl.
CPC ............ *G21F 7/045* (2013.01); *A61B 6/107* (2013.01); *G21F 1/125* (2013.01); *G21F 3/00* (2013.01); *G21F 7/03* (2013.01)

(58) Field of Classification Search
CPC . G21F 7/045; G21F 1/125; G21F 3/00; G21F 7/03; A61B 6/107

USPC ......... 250/505.1, 506.1, 507.1, 515.1, 516.1, 250/517.1, 518.1, 519.1

See application file for complete search history.

(56) References Cited

U.S. PATENT DOCUMENTS

| | | | |
|---|---|---|---|
| 4,980,564 A | 12/1990 | Steelmon | |
| 7,057,194 B2 | 6/2006 | Goldstein | |
| 8,129,702 B2 | 3/2012 | Bakker et al. | |
| 8,759,805 B2 | 6/2014 | Lambert et al. | |
| 2003/0057730 A1 | 3/2003 | De Laney | |
| 2013/0152272 A1* | 6/2013 | Schultz | G06F 3/014 2/161.6 |
| 2016/0152430 A1* | 6/2016 | Ray | A41D 19/015 242/563 |
| 2018/0009119 A1* | 1/2018 | Parrenin | B25J 21/02 |

\* cited by examiner

*Primary Examiner* — Nicole M Ippolito
(74) *Attorney, Agent, or Firm* — Kanika Radhakrishnan; Evergreen Valley Law Group

(57) ABSTRACT

Disclosed is a radiation protection barrier. The radiation protection barrier includes at least one plain panel, each including an elongate frame, and a protective sheet attached to the elongate frame. The radiation protection barrier also includes at least one interventional panel coupled to the at least one plain panel, each of the at least one interventional panel(s) including an elongate frame, a protective sheet movably arranged on the elongate frame, a pair of sterile gloves arranged at an intermediate portion of the protective sheet, and a window configured on the protective sheet under the pair of sterile gloves. The radiation protection barrier further includes a plurality of wheel arrangements coupled to the elongate frames of the at least one plain and interventional panels.

20 Claims, 3 Drawing Sheets

INTERACTIVE INTERVENTIONAL SHIELD

TECHNICAL FIELD

The present disclosure relates generally to radiology and, more particularly to, a radiation protection barrier.

BACKGROUND

Medical practitioners, involved in radiology such as fluoroscopy, interventional cardiology, interventional radiology, and neurointerventional radiology, may use x-ray imaging for various procedures. In such procedures, typically the medical practitioners wear lead or lead equivalent aprons for protecting themselves from prolonged exposure to X-rays.

Typically, such aprons weigh fifteen pounds or more. Therefore, regular and prolonged use of such aprons can create fatigue, pain, and can even lead to chronic physical ailments such as back, spine, and shoulder pain. One solution is to make the aprons lighter by using thinner layers of radiation protecting material (such as lead or lead equivalent material), but such change in density and/or atomic structure can affect the protection level offered by such aprons. Additionally, there are ceiling hanging lead or lead-equivalent aprons, but such hanging aprons can cater to only a single person and other medical practitioners involved in the radiology procedure would still need to wear conventional lead aprons. Maintaining sterility is an issue for any apparatus requiring physicians to reach through lead slits to perform a procedure on a patient.

In light of the foregoing discussion, there exists a need to overcome the aforementioned drawbacks associated with the use of lead aprons and devices used in radiology procedures.

SUMMARY

Various embodiments of the present disclosure provide a radiation protection barrier that can be used in conjunction with radiology procedures.

In an embodiment, a radiation protection barrier is disclosed. The radiation protection barrier includes at least one plain panel, each including an elongate frame, and a protective sheet attached to the elongate frame. The radiation protection barrier also includes at least one interventional panel coupled to at least one plain panel, each of at least one interventional panel includes an elongate frame, a protective sheet movably arranged on the elongate frame, a pair of sterile gloves arranged at an intermediate portion of the protective sheet, and a window configured on the protective sheet under the pair of sterile gloves. The radiation protection barrier further includes a plurality of wheel arrangements coupled to the elongate frames of at least one plain and interventional panels.

In another embodiment, a radiation protection barrier is disclosed, which includes a plain panel, having an elongate frame and a protective sheet attached to the elongate frame. The radiation protection barrier also includes an interventional panel coupled to the plain panel, the interventional panel includes an elongate frame, a protective sheet movably arranged on the elongate frame, a pair of sterile gloves arranged at an intermediate portion of the protective sheet, and a window configured on the protective sheet under the pair of sterile gloves. The radiation protection barrier further includes a plurality of wheel arrangements coupled to the elongate frames of the plain and interventional panels.

In another embodiment, a radiation protection barrier is disclosed, which includes an interventional panel having an elongate frame, a protective sheet movably arranged on the elongate frame, a pair of sterile gloves arranged at an intermediate portion of the protective sheet, and a window configured on the protective sheet under the pair of sterile gloves. The radiation protection barrier also includes a plurality of wheel arrangements coupled to the elongate frame of the interventional panel.

Other aspects and example embodiments are provided in the drawings and the detailed description that follows.

BRIEF DESCRIPTION OF THE FIGURES

For a more complete understanding of example embodiments of the present technology, reference is now made to the following descriptions taken in connection with the accompanying drawings in which.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification is not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Figure 1:
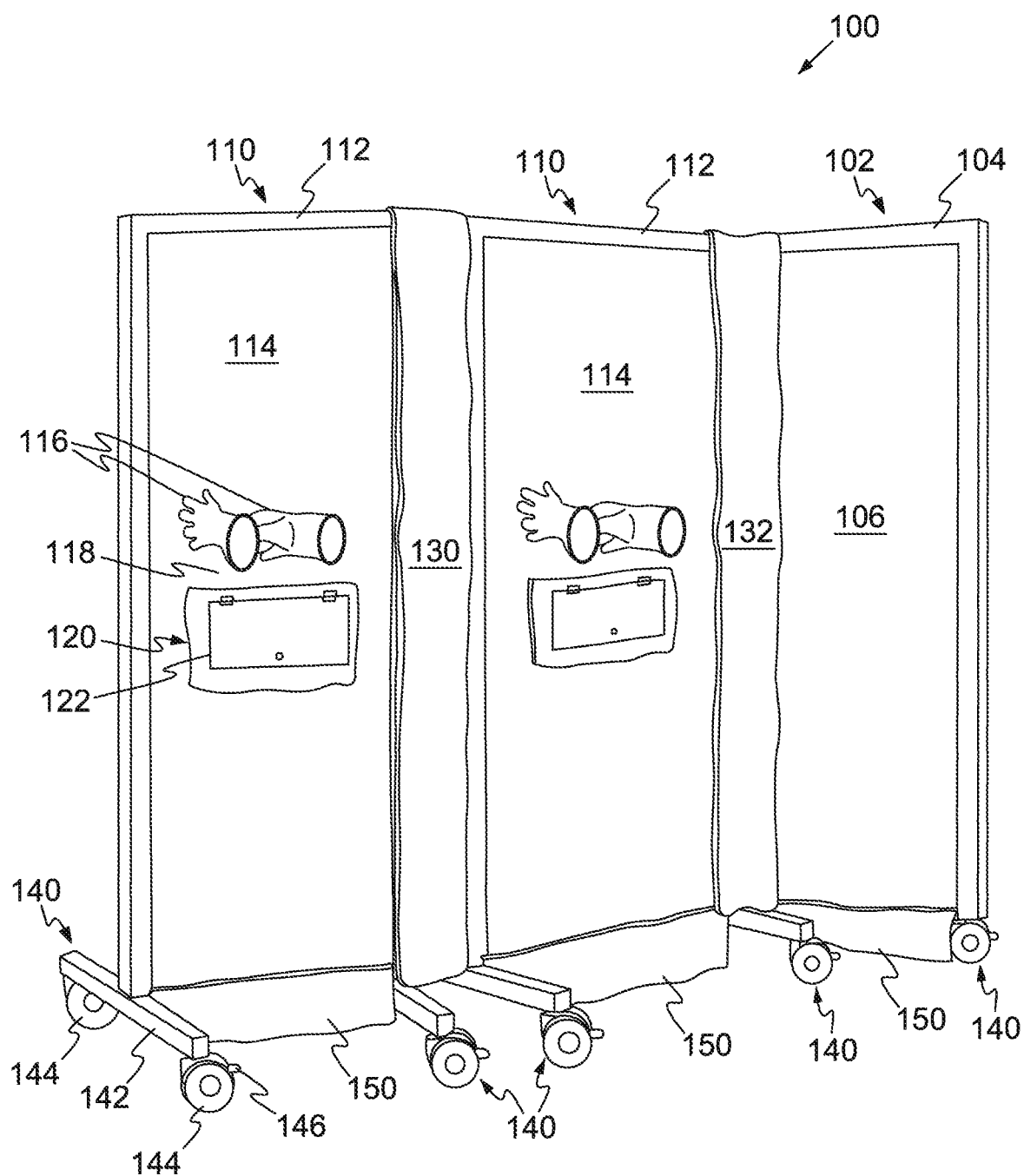
FIG. 1 is a perspective view of a radiation protection barrier, in accordance with an embodiment of the present disclosure.

Referring now to the drawings, FIG. 1 is a perspective view of a radiation protection barrier 100, in accordance with an embodiment of the present disclosure. As shown, the radiation protection barrier 100 includes at least one plain panel, such as a plain panel 102. In the present embodiment, the radiation protection barrier 100 is shown to include a single plain panel 102, however, it will be evident to those skilled in the art that the radiation protection barrier 100 may include more than one plain panel, such as two or three plain panels.

The plain panel 102 includes an elongate frame 104. In an embodiment, the elongate frame 104 is a rectangular frame made of four frame members coupled to each other. The frame members may be made of material, such as metal, plastic or any combination thereof. In an embodiment, the frame members may be made of protective material, such as lead or lead-equivalent material, explained in greater detail herein later. Further, the frame members may be hollow or solid rods coupled to each other to form the elongate frame 104. It will be evident that, a height of the elongate frame 104 would correspond to a height that is necessary to shield a medical practitioner from radiation when standing behind the radiation protection barrier 100. In an example, the elongate frame 104 may include such a length that the plain panel 102 from a ground surface offers a height of a couple of feet, such as 4 feet to 7 feet. In an example, the plain panel 102 may be configured to have a height of 6 feet. In an embodiment, the elongate frame 104 may be configured to have a fixed length to offer a non-adjustable height to the plain panel 102. Alternatively, the elongate frame 104 may be configured to have a variable length to offer adjustable height to the plain panel 102. For example, the elongate frame 104 may be configured to have a telescopic arrangement or configuration, which allows adjustable height for the plain panel 102.

The plain panel 102 includes a protective sheet 106 attached to the elongate frame 104. The term "protective sheet" used herein refers to a protective layer adapted to provide protection against radiation. The protective sheet 106 can be an integral part of the elongate frame 104, attached to the elongate frame 104, or slide into the elongate frame 104. For sterility, a sterile drape is attached across the panels with sticky strips or some other temporary manner. If the elongate frame is separate rather than an integral part of the protective sheet, the elongate frame must be long enough to support the weight of the protective sheet.

In an embodiment, the protective sheet 106 is impregnated with a protective material or contains a layer of protective material. For example, the protective sheet 106 includes (or is made solely of) a layer of protective material or made of a clear material that is impregnated with the protective material. According to an embodiment, the layer of protective material is composed of a material selected from a group consisting of Lead, Erbium, Holmium, Dysprosium, Terbium, Gadolinium, Europium, Samarium, Tantalum, Hafnium, Lutetium, Ytterbium, Thulium, Thorium, Uranium or any combination thereof. In an example, the layer of protective material includes lead or lead-equivalent material, i.e. the protective sheet 106 is solely made of lead or lead-equivalent material. Alternatively, the protective sheet 106 may be made of a clear material impregnated with the protective material, i.e. the protective sheet 106 may be made of a clear acrylic material impregnated with lead or lead-equivalent material.

According to an embodiment, the clear nature of the protective sheet 106 enables the medical practitioner to look therethrough while performing any task associated with a radiology procedure. In an alternative embodiment, with the implementation of virtual reality operating systems, which is becoming more widely available nowadays, it may not be necessary for the protective sheet 106 to be clear for allowing the medical practitioner to look therethrough. Thus, the clear nature of the protective sheet 106 is optional, and the protective sheet 106 may be configured to be unclear, i.e. when made solely of a layer of protective material.

Further, in an embodiment, the layer of protective material may include sufficient thickness that enables the protective sheet 106 to block the X-rays to pass therethrough, thereby providing radiation protection. In an example, the layer of protective material may include a thickness in a range of 2 to 5 millimeters. According to an embodiment, temporary sterile fabric attaches to the lower half of the protective sheet 106 to provide sterility during the procedure. The sterile fabric may include cotton or synthetic fabric. In an embodiment, the sterile fabric can be stick-on fabric adapted to be peelably coupled to the protective sheet 106.

The radiation protection barrier 100 also includes at least one interventional panel, such as interventional panels 110. As shown in FIG. 1, in the present embodiment, the radiation protection barrier 100 includes two interventional panels 110. However, it may be evident to those skilled in the art that the radiation protection barrier 100 may include a single interventional panel (instead of the two interventional panels 110) or more than two interventional panels, such as three interventional panels.

The interventional panels 110 are coupled to at least one plain panel, i.e. the plain panel 102. As shown, the two interventional panels 110 are laterally coupled to each other, and one of the two interventional panels 110 is further laterally coupled to the plain panel 102, which is explained in greater detail herein later.

Each of the two interventional panels 110 includes an elongate frame, such as elongate frame 112. The elongate frame 112 of the interventional panels 110 is structurally and functionally similar to the elongate frame 104 of the plain panel 102, explained herein above. For example, the elongate frame 112 is also a rectangular frame, which may be made of metal or plastic rods or protective material, and the rods may be solid or hollow. Further, a height of the elongate frame 112 would correspond to a height of the elongate frame 104. Moreover, the elongate frame 112 may be configured to have either a non-adjustable height or adjustable heights (i.e. telescopic configuration).

Each of the interventional panels 110 includes a protective sheet 114. The protective sheet 114 is impregnated with a protective material or contains a layer of a protective material. The protective sheet 114 is substantially similar to the protective sheet 106 of the plain panel 102. For example, the protective sheet 114 also includes a rectangular shape and dimensions, for example, a length and a width conforming to a length and a width of the elongate frame 112. In an embodiment, the protective sheet 114 is solely made of a layer of protective material, as explained herein above in conjunction with the plain panel 102. Alternatively, the protective sheet 114 may be made of a clear material impregnated with the protective material, i.e. made of a clear acrylic material impregnated with lead or lead-equivalent material. Additionally, according to an embodiment, a sterile drape would then be placed across the mid to bottom portion of the protective sheet 114 in order to maintain or provide sterility.

The interventional panels 110 are embedded or attached with the protective sheet 114, which is movably arranged on the elongate frame 112. The sterile drape is movably arranged across the interventional panels 110 anteriorly and posteriorly (i.e. from front and behind). According to an embodiment, each of the interventional panels 110 further includes an adjustment mechanism (not shown) for allowing the protective sheet 114 of the interventional panels 110 to move along the elongate frame 112. In an example, the adjustment mechanism may include a shaft and rollers arrangement (or a rack and pinion arrangement, not shown) mounted on the elongate frame 112, and the protective sheet 114 is arranged on the shaft and rollers arrangement in a manner such that the protective sheet 114 can move along the elongate frame 112. Further, the adjustment mechanism may be manually operated or electronically and remotely operated to allow the protective sheet 114 to move along the elongate frame 112. Additionally, it may be evident to those skilled in the art that when the elongate frame 112 is configured to have the adjustable heights (for example, by implementing telescopic arrangement) the interventional panels 110 may not include the adjustment mechanism, as explained herein above.

Each of the interventional panels 110 also includes a pair of sterile gloves 116 with customized attachment to the panel, either by a perimeter of adhesive material or by another mechanism, arranged at an intermediate portion 118 (or at a top portion) of the protective sheet 114. The pair of sterile gloves 116 may be detachably coupled to the protective sheet 114 of the interventional panels 110. For example, the protective sheet 114 may include a pair of holes (shown) and proximal ends of the pair of sterile gloves 116 are configured to be detachably attached around the pair of holes, using hook and loop fastener, adhesive and so forth. As shown, the pair of sterile gloves 116 is configured to have a shape and a size that allow a medical practitioner to insert his/her hands into the pair of sterile gloves 116 to perform any task associated with an interventional radiology procedure by standing behind the interventional panels 110. The arm length of the gloves can be customized for optimal comfort when performing the procedure behind the protective sheet. For example, the tasks may include handling interventional devices or equipment and so forth. The sterile nature of the pair of sterile gloves 116 allows the medical practitioner to effectively (i.e. in clean or germ-free manner) perform the interventional radiology procedure while still being shielded from radiation exposure. According to an embodiment, each of the pair of sterile gloves 116 is solely made of or impregnated with radiation protective material, as explained herein above. In an embodiment, each of the pair of sterile lead or lead-equivalent gloves 116 may be made of a pair of spaced apart sterile fabric, such that a layer of radiation protective material is positioned between the pair of spaced apart sterile lead or lead-equivalent fabric, and a removable sterile drape surrounds the holes for the gloves in order to maintain sterility during the procedure, as discussed herein above. In use, height of the pair of sterile gloves 116 from a ground surface can be adjusted using the adjustment mechanism arranged on the elongate frame 112 or with the help of telescopic configuration of the elongate frame 112, as explained herein above.

Each of the interventional panels 110 also includes a window 120 configured on the protective sheet 114 under the pair of sterile gloves 116. The window 120 includes a flap 122 for openably closing an opening (not shown) of the window 120. In an example, the window is created by cutting a rectangular hole in the protective sheet 114 and overlaying an oversized lead or lead-equivalent flap anterior or posterior to the window 120. The size of the flap 122 insures a radiation protective seal. A plastic sterile fabric may hug the flap 122 to maintain sterility. The window 120 is configured or arranged below the pair of sterile gloves 116. Therefore, the flap 122 may be solely made of a layer of protective material. A medical practitioner may use the window 120 to perform certain task, associated with the interventional radiology procedure, which may not be done suitably using the pair of sterile gloves 116. In an example, such tasks may include putting interventional devices on the table for the clinicians' use, such as a catheter, wire, stent, etc.

According to an embodiment, each of the plain or interventional panels 102, 110 also includes a lead or lead-equivalent roof (not shown) at an oblique angle to shield practitioners behind the radiation protection barrier 100 from scatter radiation.

As explained herein above, the two interventional panels 110 are laterally coupled to each other, and one of the two interventional panels 110 is further laterally coupled to the plain panel 102. According to an embodiment, the elongate frames 104, 112 of at least one plain panel, i.e. the plain panel 102, and the interventional panels, i.e. the interventional panels 110, are foldably coupled. The term "foldably coupled" used herein relates to coupling of the elongate frames 104, 112 of the plain panel 102 and the interventional panels 110 such that the plain panel 102 and the interventional panels 110 can be folded to be placed (or positioned) close to each other or in an overlapping state. This may help in storing the radiation protection barrier 100, when not in use, in addition to ensuring radiation protection in smaller workspaces. In an embodiment, the radiation protection barrier 100 includes intermediate protective lead or lead-equivalent strips arranged between the elongate frames to allow foldable coupling therebetween. As shown, the radiation protection barrier 100 includes intermediate protective strips 130 and 132 positioned between the two interventional panels 110, and between the plain panel 102 and one interventional panel 110, respectively. In other words, the intermediate protective strips 130, 132 are arranged (coupled or mounted) between the elongate frames 112, 112 and the elongate frames 104, 112, respectively. The intermediate protective strips 130, 132 include required flexibility to allow foldable coupling between the plain and interventional panels 102, 110. Further, it will be appreciated that the intermediate protective strips 130, 132 are also made of lead or lead-equivalent material. As mentioned herein above, the sterile drapes cross the plain or interventional panels 102, 110; therefore, the sterile drapes also cross the lower half of the intermediate protective strips 130 and 132 to maintain sterility during the procedure. The purpose of the intermediate protective strips 130, 132 is to provide a radiation protective seal for any small air gaps between the plain or interventional panels 102, 110.

According to another embodiment, the radiation protection barrier 100 may include hinges (not shown) arranged between the elongate frames to allow foldable coupling therebetween. It will be apparent to those skilled in the art that the elongate frames 104, 112 of the plain and interventional panels 102, 110 may be laterally and directly coupled in a foldable manner using long lead or lead-equivalent hinges. In such instances, the intermediate protective strips 130, 132 may not be arranged between the elongate frames 104, 112.

The radiation protection barrier 100 includes a plurality of wheel arrangements 140 coupled to the elongate frame(s) 104, 112 of the plain and interventional panels 102, 110. According to an embodiment, each of the plurality of wheel arrangements 140 includes a wheel support 142 coupled to the elongate frame, such as the elongate frames 104, 112, of the plain and interventional panels 102, 110. As shown, the wheel support 142 may be one of a solid or a hollow rod that is either made of metal or plastic. Further, the wheel support 142 may be fixedly or detachably coupled to the elongate frames 104, 112. Each of the plurality of wheel arrangements 140 also includes a pair of wheels 144 arranged on the wheel support 142. Further, each of the plurality of wheel arrangements 140 includes a stop member 146 arranged on each of the pair of wheels 144. The plurality of wheel arrangements 140 enables the movement of the radiation protection barrier 100 from one place to another, and further allows the plain and interventional panels 102, 110 to move with respect to each other to attain a folded, unfolded, or any specific position. Moreover, the stop member 146 of the plurality of wheel arrangements 140 may be used to break the pair of wheels 144 thereby allowing the radiation protection barrier 100 to have a stationary position with respect to a ground surface.

In an embodiment, the radiation protection barrier 100 further includes protective lead or lead-equivalent lower drapes 150 arranged on the elongate frames 104, 112 of the plain and interventional panels 102, 110. As shown, the protective lower drapes 150 are arranged on lower frame members (not shown) of the elongate frames 104, 112. These protective lower drapes 150 are placed at the ankle level, alleviating the need for sterility per standard operating room procedures, since they are below the level of the patient's table. The protective lower drapes 150 protect the feet of the medical practitioners from the exposure of X-rays, while allowing the medical practitioner to comfortably perform the procedure. In an embodiment, the protective lower drapes 150 may be solely made of a layer of protective material.

Figure 2:
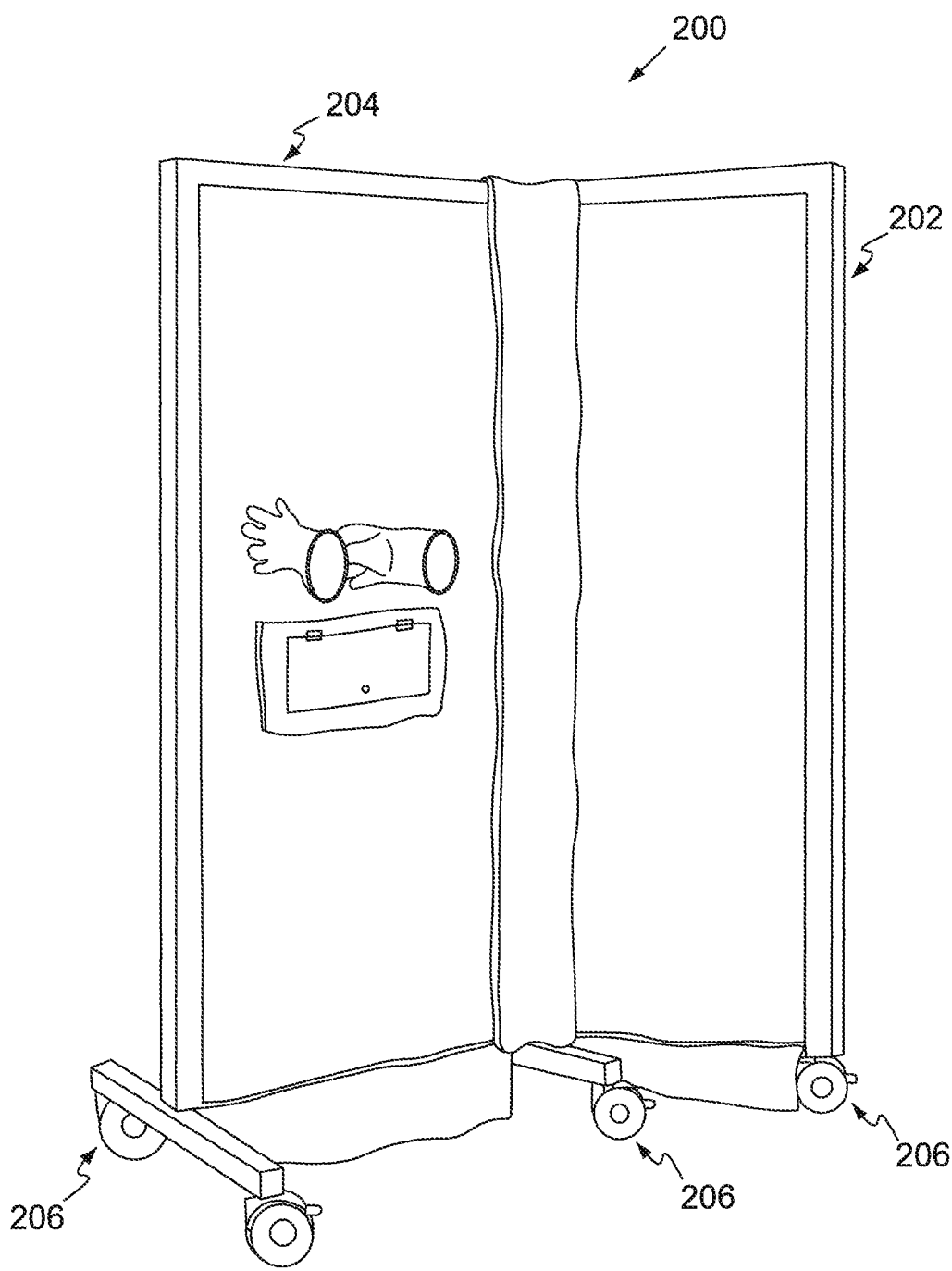
FIG. 2 is a perspective view of a radiation protection barrier, in accordance with another embodiment of the present disclosure.

Referring now to FIG. 2, illustrated is a perspective view of a radiation protection barrier 200, in accordance with another embodiment of the present disclosure. As shown, the radiation protection barrier 200 is substantially similar to the radiation protection barrier 100, explained in conjunction with FIG. 1. For example, the radiation protection barrier 200 includes a plain panel 202 and an interventional panel 204 coupled to the plain panel 202. The plain and interventional panels 202, 204 are structurally and functionally similar to the plain and interventional panels 102, 110, respectively, of the radiation protection barrier 100. The radiation protection barrier 200 also includes a plurality of wheel arrangements 206, similar to the plurality of wheel arrangements 140, coupled to elongate frames of the plain and interventional panels 202, 204. It will be apparent to a person skilled in the art that the text explaining the plain and interventional panels 202, 204 and the plurality of wheel arrangements 140 is avoided for the purpose of brevity.

Figure 3:
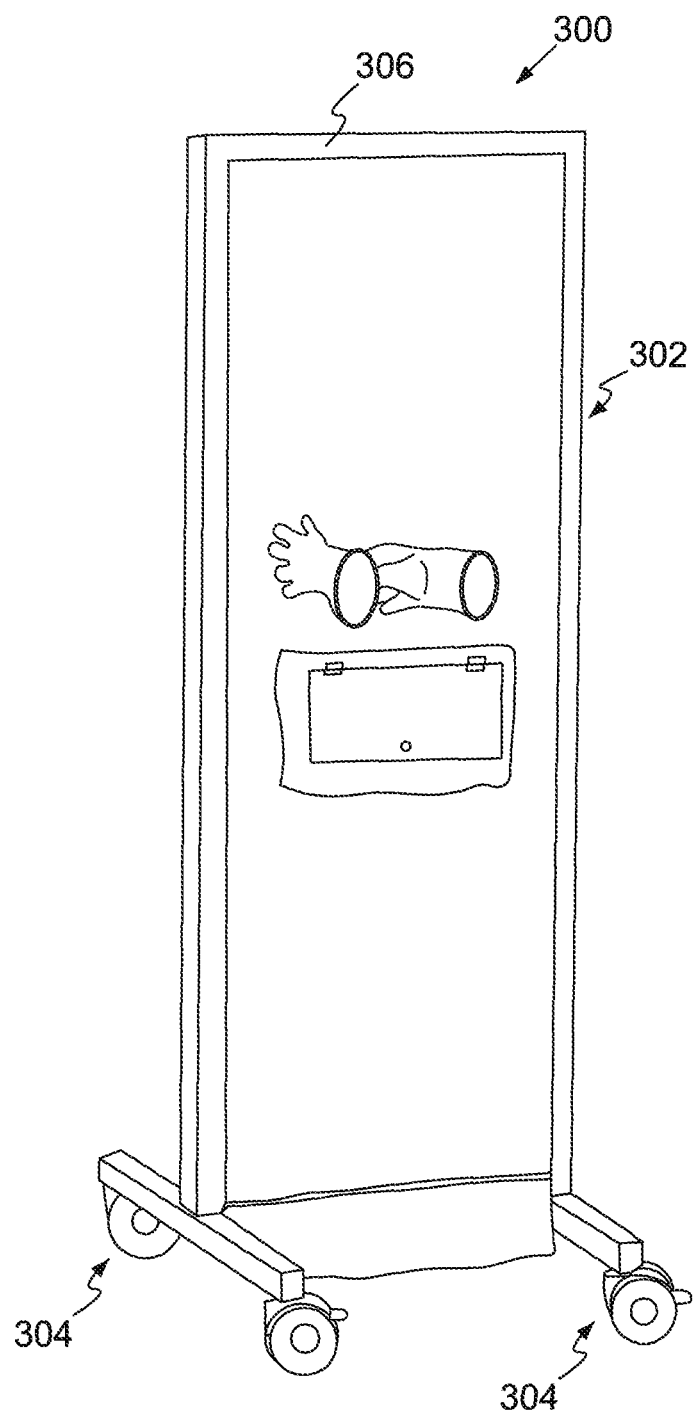
FIG. 3 is a perspective view of a radiation protection barrier, in accordance with yet another embodiment of the present disclosure.

Referring now to FIG. 3, illustrated is a perspective view of a radiation protection barrier 300, in accordance with yet another embodiment of the present disclosure. As shown, the radiation protection barrier 300 is substantially similar to the radiation protection barrier 100, explained in conjunction with FIG. 1. For example, the radiation protection barrier 300 also includes an interventional panel 302 (such as the interventional panel 110) and a plurality of wheel arrangements 304 (such as the plurality of wheel arrangements 140) coupled to an elongate frame 306 of the interventional panel 302. The width of the panel may be extended to the dimension necessary to insure radiation safety of the operator and assisting staff at the interventional table. It will be apparent to a person skilled in the art that the text explaining the interventional panel 302 and the plurality of wheel arrangements 304 is avoided for the purpose of brevity.

Embodiments of the present disclosure substantially eliminate or at least partially address the aforementioned problems in the background and provide a radiation protection barrier. The radiation protection barrier enables medical practitioners to avoid wearing heavy lead or lead equivalent aprons, thereby avoiding chronic physical ailments such as back, spine, and shoulder pain, which can arise from prolonged use of such heavy aprons. The radiation protection barrier provides the required protection from X-ray radiation, as there is no need to compromise at the structural (i.e. thickness) level of the radiation protecting material that will be used to make the radiation protection barrier. Further, the radiation protection barrier of the present disclosure can be simultaneously used by multiple medical practitioners involved in any radiology procedure. Moreover, the radiation protection barrier is specifically designed for use in sterile settings, which is necessary for performing interventional radiology procedures, such as those related to interventional cardiology, interventional radiology, neurointerventional radiology, and so forth. Further in use, when the medical practitioner removes his/her hands from the sterile lead or lead-equivalent gloves, the medical practitioner will have sterile non-lead gloves underneath, which can be used to collect devices off a sterile table and pass the devices to be applied on a patient's body through the window, while the fluoroscopy machine is in off mode. The radiation protection barrier of the present disclosure creates a radiation free zone for a supporting technician or attendant who can stand at the table preparing devices later applied to the patient. A nurse can comfortably monitor vitals of the patient from behind the radiation protection barrier. Medications can be administered from a long IV line placed behind the radiation protection barrier and outside of the sterile field so that the nurse can maintain his/her position.

The embodiments illustrated and described herein as well as embodiments not specifically described herein but within the scope of the aspects of the invention constitute an exemplary radiation protection barrier.

The benefits and advantages described above may relate to one embodiment or may relate to several embodiments. The embodiments are not limited to those that solve any or all of the stated problems or those that have any or all of the stated benefits and advantages.

Aspects of any of the examples described above may be combined with aspects of any of the other examples described to form further examples without losing the effect sought.

The above description is given by way of example only and various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

What is claimed is:
1. A radiation protection barrier comprising:
  at least one plain panel, each comprising:
    an elongate frame, and
    a protective sheet attached to the elongate frame;
  at least one interventional panel coupled to at least one plain panel, each of at least one interventional panel comprising:
    an elongate frame,
    a protective sheet movably arranged on the elongate frame, a pair of sterile gloves arranged at an intermediate portion of the protective sheet, and a window configured on the protective sheet under the pair of sterile gloves; and a plurality of wheel arrangements coupled to the elongate frames of the at least one plain and interventional panels.

2. The radiation protection barrier as claimed in claim 1, wherein the elongate frames of the at least one plain and interventional panels are foldably coupled.

3. The radiation protection barrier as claimed in claim 2, further comprising intermediate protective lead or lead-equivalent strips arranged between the elongate frames to allow foldable coupling therebetween.

4. The radiation protection barrier as claimed in claim 2, further comprising hinges arranged between the elongate frames to allow foldable coupling therebetween.

5. The radiation protection barrier as claimed in claim 1, further comprising protective lower lead or lead-equivalent drapes arranged on the elongate frames of the at least one plain and interventional panels.

6. The radiation protection barrier as claimed in claim 1, wherein the window comprises a flap for closing and opening of the window.

7. The radiation protection barrier as claimed in claim 1, wherein each of the plurality of wheel arrangements comprises:
    a wheel support coupled to the elongate frame of the at least one plain and interventional panels;
    a pair of wheels arranged on the wheel support; and
    a stop member arranged on each of the pair of wheels.

8. The radiation protection barrier as claimed in claim 1, wherein at least one interventional panel further comprises an adjustment mechanism for allowing the protective sheet of the at least one interventional panel to move along the elongate frame thereof.

9. The radiation protection barrier as claimed in claim 1, wherein the protective sheet and the pair of sterile gloves are impregnated with a protective material or contain a layer of the protective material.

10. The radiation protection barrier as claimed in claim 9, wherein the layer of protective material is composed of a material selected from a group consisting of: Lead, Erbium, Holmium, Dysprosium, Terbium, Gadolinium, Europium, Samarium, Tantalum, Hafnium, Lutetium, Ytterbium, Thulium, Thorium, Uranium or any combination thereof.

11. A radiation protection barrier comprising:
    a plain panel comprising:
        an elongate frame, and
        a protective sheet attached to the elongate frame;
    an interventional panel coupled to the plain panel, the interventional panel comprising:
        an elongate frame,
        a protective sheet movably arranged on the elongate frame,
        a pair of sterile gloves arranged at an intermediate portion of the protective sheet, and
        a window configured on the protective sheet under the pair of sterile gloves; and
    a plurality of wheel arrangements coupled to the elongate frames of the plain and interventional panels.

12. The radiation protection barrier as claimed in claim 11, wherein the elongate frames of the plain and interventional panels are foldably coupled.

13. The radiation protection barrier as claimed in claim 12, further comprising intermediate protective lead or lead-equivalent strips or hinges arranged between the elongate frames to allow foldable coupling therebetween.

14. The radiation protection barrier as claimed in claim 11, further comprising protective lower lead or lead-equivalent drapes arranged on the elongate frames of the plain and interventional panels.

15. The radiation protection barrier as claimed in claim 11, wherein the window comprises a flap for closing and opening of the window.

16. The radiation protection barrier as claimed in claim 11, wherein each of the plurality of wheel arrangements comprises:
    a wheel support coupled to the elongate frame of the plain and interventional panels;
    a pair of wheels arranged on the wheel support; and
    a stop member arranged on each of the pair of wheels.

17. The radiation protection barrier as claimed in claim 11, wherein the interventional panel further comprises an adjustment mechanism for allowing the protective sheet of the interventional panel to move along the elongate frame thereof.

18. The radiation protection barrier as claimed in claim 11, wherein the protective sheet and the pair of sterile gloves are impregnated with a protective material or contain a layer of the protective material.

19. The radiation protection barrier as claimed in claim 18, wherein the layer of protective material is composed of a material selected from a group consisting of: Lead, Erbium, Holmium, Dysprosium, Terbium, Gadolinium, Europium, Samarium, Tantalum, Hafnium, Lutetium, Ytterbium, Thulium, Thorium, Uranium or any combination thereof.

20. A radiation protection barrier comprising:
    an interventional panel comprising:
        an elongate frame,
        a protective sheet movably arranged on the elongate frame,
        a pair of sterile gloves arranged at an intermediate portion of the protective sheet, and
        a window configured on the protective sheet under the pair of sterile gloves; and
    a plurality of wheel arrangements coupled to the elongate frame of the interventional panel.

\* \* \* \* \*